United States Patent [19]
Lee

[11] Patent Number: 5,092,344
[45] Date of Patent: Mar. 3, 1992

[54] REMOTE INDICATOR FOR STIMULATOR

[76] Inventor: Tzium-Shou Lee, 924 Maple Rd., Flossmoor, Ill. 60422

[21] Appl. No.: 615,339

[22] Filed: Nov. 19, 1990

[51] Int. Cl.⁵ .............................................. A61B 5/05
[52] U.S. Cl. ...................................................... 128/741
[58] Field of Search ............... 128/421, 741, 795, 796, 128/802

[56] References Cited

U.S. PATENT DOCUMENTS

| | | | |
|---|---|---|---|
| 3,682,162 | 8/1972 | Colyer | 128/741 |
| 3,898,983 | 8/1975 | Elam | 128/741 |
| 4,197,641 | 4/1980 | Paulke et al. | 128/741 |
| 4,387,723 | 6/1983 | Atlee | 128/741 |
| 4,515,168 | 5/1985 | Chester et al. | 128/741 |
| 4,962,766 | 10/1990 | Herzon | 128/741 |

OTHER PUBLICATIONS

Neuro Technology, Inc., "Instruction Manual for Digistim III P/N 10021", 1986.

*Primary Examiner*—Max Hindenburg
*Attorney, Agent, or Firm*—Hill, Van Santen, Steadman & Simpson

[57] ABSTRACT

An indicator for a nerve stimulator located remotely from the pulse generator and secured onto the precise portion of the anatomy under observation for responsive twitch. The indicator comprises exemplary embodiments of visual annunciators including a light bulb, a light emitting diode, a liquid crystal diode, or other visual indications. A wrap arrangement holds the indicator to the observed part of the anatomy such as a finger. Alternately, a finger cap attachment provides a convenient means to attach the annunciator to a finger under observation. A needle probe can be used for mounting the annunciator to internal areas of the anatomy. A second exemplary embodiment of the indicator provides that the annuciator is mounted to a needle probe wherein the indicator signal and the pulse are directed to the same location of the anatomy, and where the annunciator is mounted to a free end of the needle probe, twitching of the flesh at the probe sight is readily visible by movement of the annunciator in synchronization with the flashing annunciator. As an alternative to the visible indicators, an audible annuciator, such as a sound emitting transducer, can be locally mounted to the part of the anatomy under observation.

13 Claims, 1 Drawing Sheet

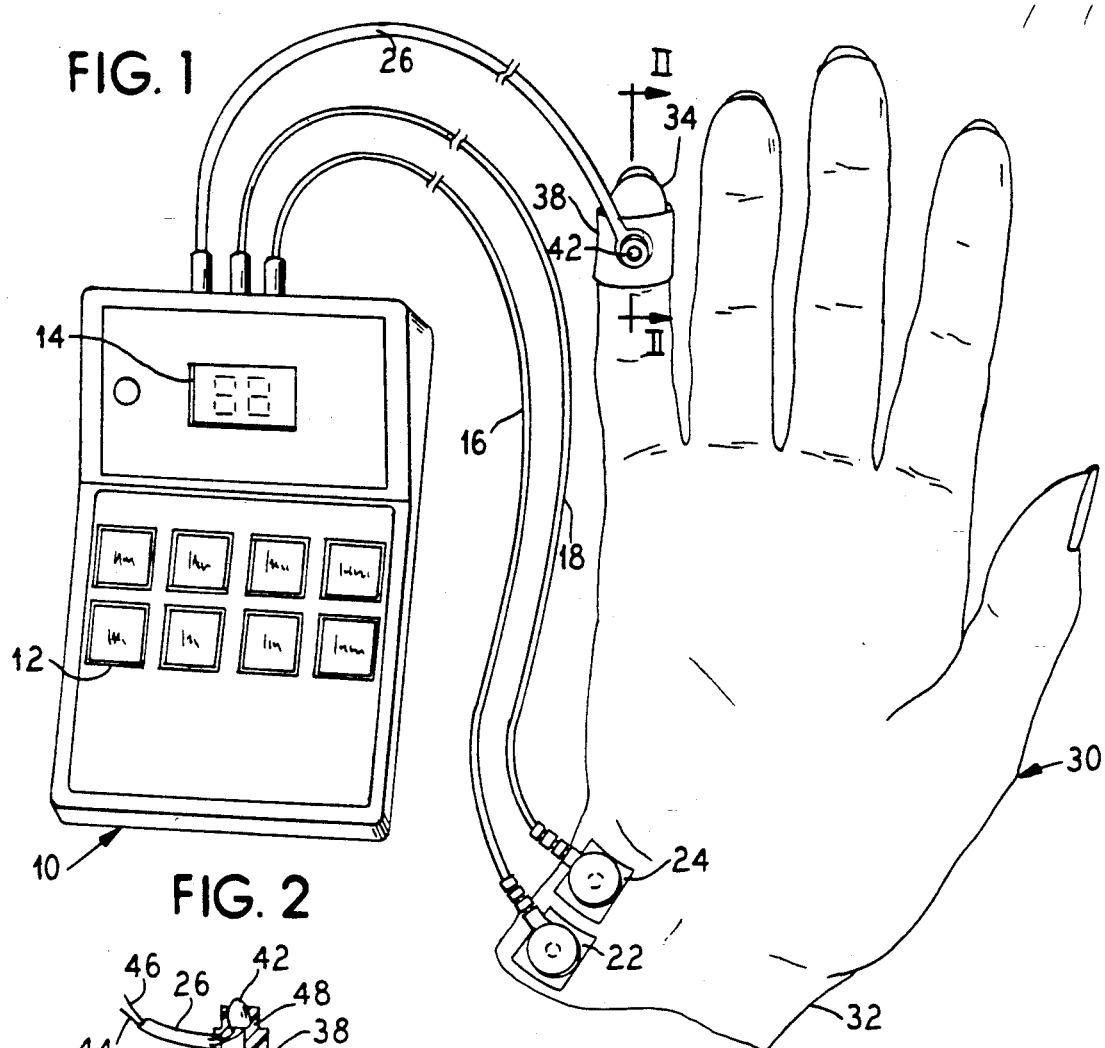
FIG. 1
FIG. 2
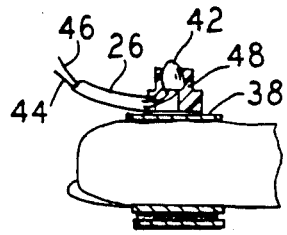
FIG. 3
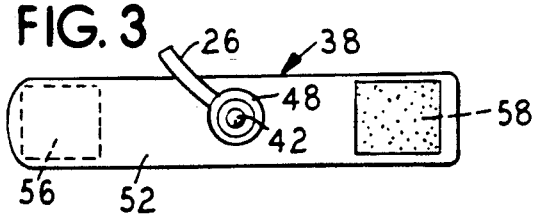
FIG. 4
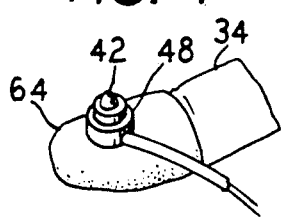
FIG. 5
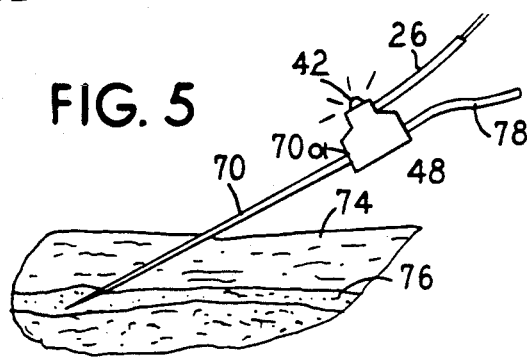

REMOTE INDICATOR FOR STIMULATOR

BACKGROUND OF THE INVENTION

During normal anesthesia, and particularly when muscle relaxants are utilized, a nerve or muscle stimulator is utilized to impose a muscle twitch as a means of determining the current effectiveness of the medication on the patient. Such nerve or muscle stimulators are variously called "muscle relaxant indicators" or "nerve stimulators" or "nerve locators" and are commonly available and include generator units that produce timed electrical pulses that can be used to stimulate a nerve or a muscle. Various such devices utilize both audible and visual indicators for the electric pulse. A typical nerve stimulator is the Norcuron ® peripheral nerve stimulator, manufactured for Organon Inc., West Orange, N.J. 07052 by Neuro Technology of Houston, TX. However, in current devices both the audible and visual indicators are located at the generator unit. The generator unit may be a hand-held battery powered unit wherein the anesthesiologist's attention is directed to the activated end of the muscle.

The muscle, when energized by the pulse, will, unless completely sedated, twitch. The anesthesiologist is therefore focusing on the appropriate anatomical location for indications of twitch. Because it is desired to detect the early onset of muscle movement, the actual twitch may be quite faint. That is, the movement may be very small. In order to distinguish from non-stimulated movements that might occur, it is necessary for the anesthesiologist to detect the pulse induced movements only. To do this the anesthesiologist must correlate the timing of the induced pulse, to the actual movement that occurs either by listening for the audible indicator or by watching the visual indicator. Because the buzzer is very faint, it frequently cannot be heard in the operating room. Making a louder buzzer may not be practical in an operating room where the repeated triggering of the pulse would disrupt communication and provide an annoying background. It is also very complex to watch both the visual indicator at the generator unit and the anatomical spot under observation.

SUMMARY OF THE INvENTION

It is an object of the present invention to provide a secondary location for the above described visual indicator or audible indicator. A generator or nerve stimulator would be provided with a remote visual indicator or audible indicator that can be located directly at the anatomical spot under observation. In the first embodiment, the remote visual indicator, which could be a small light bulb, a light emitting diode, a liquid crystal diode or a similar visual tell-tale that can have an on/off condition timed to the pulse generation, could, for example, be attached directly to a finger of a patient with the stimulator attached adjacent the muscle or nerve controlling movement of that finger. A standard location site corresponding to this arrangement is to introduce the pulse in the wrist area overlying the appropriate anatomical site as to cause the small finger to twitch. In that example, a light indicating device would, therefore, also be attached adjacent the end of the finger. This attachment can either be by a small cap or band that can be slipped over the finger end and which has the light indicator attached thereon, or some other suitable means of attachment such as a small adhesive patch.

Because these nerve stimulator devices are sometimes used where actual direct visual observation is not convenient, such as muscles on the inside of the cheek or in the throat or muscles buried deeper in the anatomy where external visual indication is not facilitated, it has also been known to use probe needles where a needle or probe may be buried in the patient's muscle and muscle twitch thereafter notice by observing movement of the projecting needle or probe end. In this second embodiment, the remote light can be mounted at the needle end. This is particularly useful in those instances where the movement of the probe might otherwise be small. By attaching the visual indicator to the end of the probe, it will be easier to detect minor movements of the probe since the visual indicator itself will be moving as it is illuminated. The probe can also be used to transmit the pulse at the same anatomical spot.

In both these examples the location of a visual indicator at the sight of the twitch can provide two advantages: the first advantage is that the pulse indication is located in the same field of view as the anatomical part under observation; and the second advantage is that the light itself helps visually emphasize or exaggerate subtle or small movements making observation of such movements more readily achievable.

In another embodiment the annunciator is an audible indicator which is located at the spot of observation. This is an improvement on the remote prior art audible signals which, by being at a remote location from the sport under observation, can make synchronization of the twitch and the audible signal difficult. Modern sound emitting transducers mounted at the spot under observation can be made highly directional so that the audible signal is not "lost" in the operating room.

BRIEF DESCRIPTION OF THE DRAWINGS

FIG. 1 is a perspective view of a nerve stimulator wired to a patient's hand and wrist in accordance with the invention;

FIG. 2 is a partial sectional drawing generally along line II—II of FIG. 1;

FIG. 3 is a plan drawing of an attachment wrap for the pulse indicator of the present invention, in an unwrapped condition;

FIG. 4 is a perspective view of an alternate embodiment of the pulse indicator wherein the pulse indicator is attached to a finger using a finger cap; and FIG. 5 is a sectional view of a second alternate embodiment of the pulse indicator wherein the pulse indicator is mounted onto a free end of a probe needle, the probe needle penetrating into the anatomy under observation.

DETAILED DESCRIPTION OF THE PREFERRED EMBODIMENTS

FIG. 1 shows a nerve stimulator 10 comprising a control panel 12 for adjusting the intensity, duration, and period between pulses, of the generated pulse. A readout indicator 14 indicates the intensity. Pulse leads 16, 18 terminating in electrodes 22, 24 deliver a selected pulse to the patient. An indicator lead 26 connects the nerve stimulator 10 to an annunciator 42 mounted in a socket 48 carried by a pulse indicator wrap 38 which mounts to the patient's finger 34 or other area to be observed.

In an example of the invention the pulse leads 22, 24 generate a pulse in the vicinity of the nerve which controls movement of the small finger 34 on the patient's hand 30. When the selected pulse is generated, a simultaneous signal such as an electric signal is transmitted through the indicator lead 26 to trigger the annunciator 42. The annunciator 42 can be a light bulb, or other visual means such as an LED (light emitting diode), a LCD (liquid crystal diode), an incandescent bulb, or a visible terminal end of a light conducting fiber. In the latter case, the lead 26 is a light conducting fiber. Also, alternatively, the annunciator can generate an audible signal such as created by a sound emitting transducer.

Thus, when the anesthetic is beginning the wear off in effect on the patient, pulses generated to the nerve in the vicinity of the wrist 32 will begin to trigger subtle twitching in the small finger 34 of the patient. The anesthesiologist will be able to correlate the subtle twitching in the small finger 34 with the indications of the annunciator 42 to distinguish random movement of the small finger from the twitching generated by the nerve stimulator.

FIG. 2 shows the indicator lead 26 comprising two electrical conductors 44, 46 which carry the electrical circuit through the annunciator 42, such as a light bulb. The light bulb is fixed into the socket 48 which is mounted onto the indicator wrap 38 such as by adhesive.

FIG. 3 shows the indicator wrap 38 comprising a elongated rectangular panel 52 with two patches of fastening material 56, 58 applied on opposite face sides of the panel 52 and at opposite ends of the panel 52. A material such as Velcro, or a sticky adhesive can be utilized for wrapping and fastening of the indicator wrap at the connecting materials 56, 58.

FIG. 4 shows an alternate embodiment of the indicating wrap 38. A finger cap 64 forming a hood-like or thimble-like cover to an end of the finger 34 to be observed holds thereon the socket 48 holding the annunciator 42. The embodiment of FIG. 4 comprises a convenient and quickly mounted carrier for the annunciator 42.

FIG. 5 shows a second alternate embodiment of the pulse indicator which is particularly useful for probing areas to determine nerve response. A probe 70 is inserted beneath the skin 74 to probe for nerve areas such as 76. The probe 70 carries at its free end 70a the socket 48 holding the annunciator 42 which is wired to the pulse indicating lead 26. In this illustration, a pulse generating cable 78 is connected through the socket 48 to the probe 70 for generating a pulse through the probe and into the nerve area 76. However, as shown in FIG. 1, the actual pulse can be applied to a remote anatomical area; in such case no cable 78 need be connected to the probe 70. Any twitching of the area upon application of the electrical pulse through the probe 70, or remotely, will be readily observed by movement of the annunciator 42 cantilevered at the free end 70a of the probe, synchronized with the actuation or indication of the annunciator 42. The location of the annunciator 42 at the free end 70a of the elongated probe 70 tends to amplify the displacement of the twitch at the annunciator 42. Also, in the case of an illuminated annunciator small movement is further emphasized or "picked up" visually. Thus, the twitch is easier to observe.

It is conceived by the inventor that the lead 26 could be replaced by a wireless transmitted signal received by the annunciator and such is encompassed by the invention. it is conceived by the inventor that other means could be utilized to stimulate the patient, replacing the electrodes 22, 24 or the probe 70, in conjunction with Applicant's remote indicator and such systems are encompassed by the invention.

Although the present invention has been described with reference to a specific embodiment, those of skill in the art will recognize that changes may be made thereto without departing from the scope and spirit of the invention as set forth in the appended claims.

I claim as my invention:

1. A remote indicator for a nerve stimulator generator wherein the nerve stimulator generator provides electric pulses to a first part of a patient's anatomy to observe a resultant twitching movement of a second part of the patient's anatomy, comprising:
   an annunciator providing a noticeable indication when activated;
   a means for mounting said annunciator to said second part of said anatomy;
   a means for communicating a signal to activate said annunciator for noticeable indication, synchronized with said electric pulses.

2. A remote indicator according to claim 1, wherein said means for communicating said signal comprises a lead connecting said signal generator to said annunciator, said lead carrying said signal.

3. A remote indicator according to claim 2, wherein said annunciator comprises a light element and said lead comprises a pair of electrical conductors carrying said signal.

4. A remote indicator according to claim 2, wherein said annunciator comprises a light emitting diode and said lead comprises a pair of electrical conductors.

5. A remote indicator according to claim 2, where said annunciator comprises a liquid crystal diode.

6. A remote indicator according to claim 2, wherein said annunciator comprises a visible terminal end of a light conducting fiber and said lead comprises a light conducting fiber.

7. A remote indicator according to claim 1, wherein said means for mounting comprises a wrap-like panel having at least one attachment portion applied on a first portion of said panel, said wrap-like panel wrapped around said second part of said anatomy, said attachment portion engaging a second portion of said panel to capture said second part of said anatomy therein.

8. A remote indicator according to claim 1, wherein said means for mounting comprises a finger cap, and said second part of said anatomy comprises a patient's finger, said finger cap fitting over an end portion of said finger, said annunciator fixed to an outside of said finger cap.

9. A remote indicator according to claim 1, wherein said means for mounting said annunciator to said second part of said anatomy is a needle probe penetrating the patient's anatomy.

10. A remote indicator according to claim 1, wherein said annunciator comprises a sound emitting transducer.

11. A combination annunciator and probe for a remotely located nerve stimulator generator wherein the nerve stimulator generator provides a stimulation signal, comprising:
   a probe for transmitting said stimulation signal to a location of the patient's anatomy;
   an annunciator mounted to said probe, said annunciator when activated, providing a visual signal;

a lead connecting said remote nerve stimulator generator to said probe, said lead providing the stimulation signal to said probe; and a signal lead from said nerve stimulator generator providing an indication signal to activate said annunciator, said indication signal synchronized with said stimulation signal.

12. A combination probe annunciator according to claim 11, wherein said probe comprises a needle probe which can be partially inserted beneath an outside layer of the patient's anatomy.

13. A combination probe annunciator according to claim 12, wherein said annunciator comprises a light element mounted in a socket, said socket mounted to a free end of said needle probe, said indicator lead providing a pair of conductors for energizing said light element, and said socket providing an electrical connection between said pulse lead and said needle probe.

* * * * *